United States Patent [19]

Scot et al.

[11] Patent Number: 5,001,436

[45] Date of Patent: Mar. 19, 1991

[54] DEVICE FOR MEASURING THE WATER CONTENT OF A SUBSTRATE, IN PARTICULAR THE SKIN

[75] Inventors: Jean Scot, Paris; Roland Bazin, Vitry S/Seine; Jean-Luc Leveque, Le Raincy, all of France

[73] Assignee: L'Oreal, Paris, France

[21] Appl. No.: 329,209

[22] Filed: Mar. 27, 1989

[30] Foreign Application Priority Data

Mar. 25, 1988 [FR] France .................. 88 03937

[51] Int. Cl.$^5$ ............................................ G01R 27/26
[52] U.S. Cl. ..................... 324/689; 324/611; 324/664; 324/692; 324/694; 324/696
[58] Field of Search ............... 324/664, 665, 689, 692, 324/694, 696, 688, 611

[56] References Cited

U.S. PATENT DOCUMENTS

| | | | |
|---|---|---|---|
| 3,870,951 | 3/1975 | Brown et al. | 324/689 |
| 4,176,555 | 12/1979 | Dorman | 324/388 X |
| 4,311,959 | 1/1982 | Riessland et al. | 324/688 X |
| 4,403,215 | 9/1983 | Hofmann et al. | 324/692 X |
| 4,551,785 | 11/1985 | Kröner | 324/688 X |
| 4,568,873 | 2/1986 | Oyanagi et al. | 324/688 X |
| 4,692,685 | 9/1987 | Blaze | 324/692 |

FOREIGN PATENT DOCUMENTS 1598910 5/1970 Fed. Rep. of Germany .
1265357 5/1961 France .
2266882 4/1974 France .

OTHER PUBLICATIONS

Medical & Biological Engineering & Computing, vol. 24, No. 1, Jan. 1986, pp. 71-77, Yamamoto et al: "Characteristics of Skin Admittance for Dry Electrodes and the Measurement of Skin Moisturization".

Primary Examiner—Reinhard J. Eisenzopf
Assistant Examiner—Robert W. Mueller
Attorney, Agent, or Firm—Cushman, Darby & Cushman

[57] ABSTRACT

The device comprises: a high frequency alternating voltage generator the output of which is connected to a sensor probe 5 which is to be applied to a substrate to be measured, an amplifier the input of which is connected to the sensor probe, and a detector arranged to furnish a D.C. voltage signal based on the output from amplifier. The generator, the amplifier and the detector are located inside a metal envelope enclosure. An electromagnetic radiation shield is disposed inside the envelope to separate the amplifier and the detector from the high frequency generator. In operation, voltage output from the detector is indicative of the electrical impedance of the substrate as sensed at the probe. In the preferred application, the substrate is skin and the measured electrical impedance is indicative of the water content of the skin.

13 Claims, 1 Drawing Sheet

DEVICE FOR MEASURING THE WATER CONTENT OF A SUBSTRATE, IN PARTICULAR THE SKIN

FIELD OF THE INVENTION

The invention relates to a device for measuring the water content of a substrate. The device is of the type including: an alternating voltage generator the output of which is connected to a sensor probe intended to be applied to the substrate, an amplifier the input of which is connected to the sensor probe, and a detection means arranged to furnish a D.C. voltage signal based on the output signal of the amplifier. The level of this D.C. voltage signal is indicative of the water content of the substrate.

More particularly, the invention relates to a device for measuring the water content of human skin.

BACKGROUND OF THE INVENTION

Devices proposed thus far, although they do to some degree indicate water content, do not produce sufficiently reliable results. Two prior art devices measuring the water content in a single substrate may well indicate very different contents.

SUMMARY OF THE INVENTION

A first object of the invention is to reduce substantially such disparities in the measurement of different devices on the same substrate. In other words, a good correspondence between the water content of the substrate and the measurements obtained from the device is sought.

Another object of the invention is to furnish a device with which measurement are performed in a simple manner, with a sensor that is easy to use, and which measure water content at a significant depth into the substrate.

The invention for measuring the water content of a substrate has a generator, an amplifier, and a detection means, all of which are disposed inside a metal envelope. The generator is a high-frequency alternating voltage generator an electromagnetic radiation shield or screen is disposed in the envelope to separate the amplifier and the detection means from the generator. A sensor probe is located at one end of the envelope and is connected both to the output of the generator and to the input of the amplifier.

The frequency of the generator is greater than 100 kHz, preferably on the order of 10.7 MHz. The amplitude and frequency of the signal output from the signal generator is unaffected by variations in the magnitude of our output by the generator. Preferably, this generator is connected at its output, via a resistor, to the sensor probe. The resistance of this resistor is selected to be sufficiently high to provide correct insulation of the voltage generator and sufficiently low to enable obtaining a sufficient signal at the input of the amplifier. This resistance is optimally on the order of 1 kiloohm.

The amplifier is selected to have a high input impedance so as not to affect the voltage at the probe. This input impedance is optimally on the order of 100 kiloohms.

The metal envelope in which the voltage generator, the amplifier, and the detection means are accommodated is preferably in the form of a cylinder. The electromagnetic radiation shield or screen disposed in this envelope comprises a metal plate. This plate is located in a diametral plane of this cylinder to divide the internal volume of the envelope into two half-cylinders. The high-frequency generator is located in one of these half-cylinders, while the amplifier and the detection means are located in the other half-cylinder.

Besides the features described above, the invention comprises a certain number of other features, described in further detail below in terms of an exemplary, but in no way limiting, embodiment described in the drawings.

DESCRIPTION OF THE PREFERRED EMBODIMENT

Figure 1:
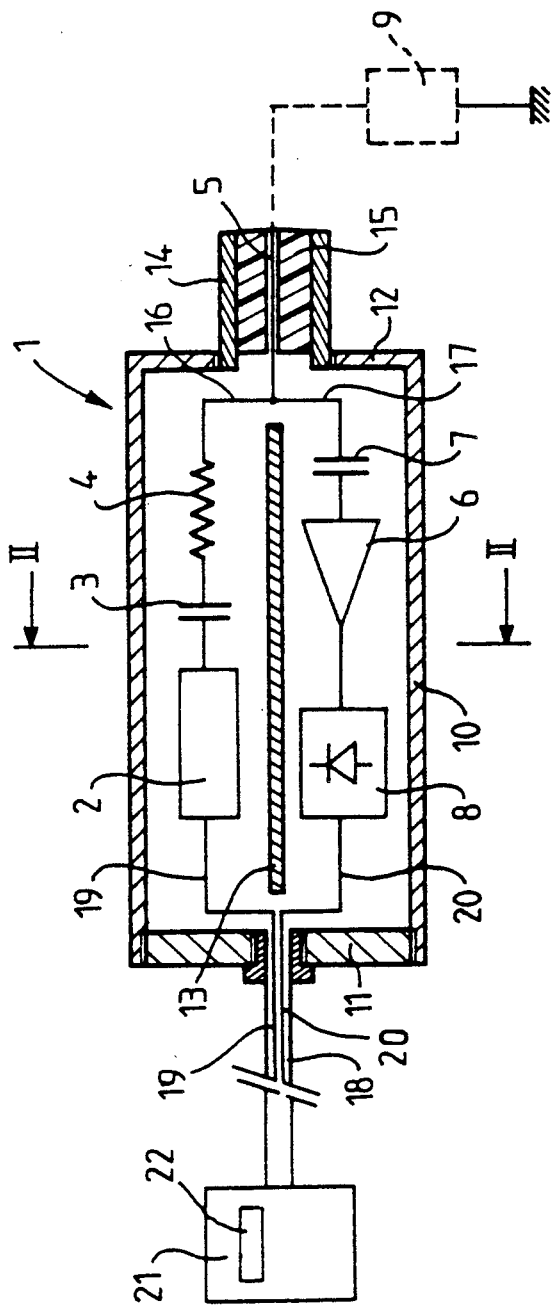
FIG. 1 is a schematic longitudinal section through a device according to the invention.
Figure 2:
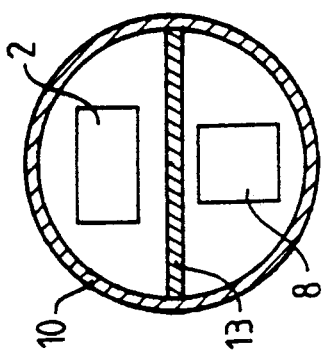
FIG. 2 is a section taken along the lines II—II of FIG. 1.

FIG. 1 shows a device 1 for measuring the water content of a substrate, in particular of human skin. This device includes a generator 2 which outputs a high-frequency alternating voltage signal of a frequency greater than 100 kHz. Preferably this frequency is 10.7 MHz. The output of generator 2 is connected via a capacitor 3 and a resistor 4 to a sensor probe 5. Probe 5 comprises a metal rod or stylus which is intended to be placed in contact with the substrate. The generator 2 is an alternating voltage generator whose output voltage amplitude and frequency are unaffected by the magnitude of current output by generator 2.

The device 1 also includes an amplifier 6, the input of which is connected via a capacitor 7 to the sensor probe 5. The amplifier 6 has a high input impedance on the order of 100 kiloohms so that it does not affect the measurement on probe 5.

Detection means 8, the input of which is connected to the output of the amplifier 6, is provided to furnish a D.C. voltage signal based on the signals coming from the amplifier.

When the sensor probe 5 is put in contact with the substrate, in particular the skin, from an electrical point of view, the end of the probe 5 is connected to ground via an impedance 9. The value of this impedance depends on the water content of the substrate. The level of the D.C. voltage signal on the output of the detection means 8, therefore also depends on the value of the impedance 9 and hence on the water content of the substrate.

Voltage generator 2, amplifier 6, and detection means 8 are accommodated inside a metal envelope 10. The metal envelope 10 takes the form of a cylinder closed at its two longitudinal ends by transverse walls 11, 12. These walls are also metal. An electromagnetic radiation screen 13 disposed in the envelope 10 separates amplifier 6 and detection means 8 from the high-frequency generator 2. This screen 13 comprises a metal plate, disposed and fixed along a diametral plane of the metal envelope 10, which is thus divided into two half-cylinders. The generator 2 is located in one of these half-cylinders, while the amplifier 6 and detection means 8 are located in the other half-cylinder. The envelope 10 and the screen 13 can be made of a lightweight alloy, in particular an aluminum-based alloy.

Sensor probe 5 is formed by a rod located at one end of the envelope 10. This rod lengthens along its axis orthogonal to the wall 12. The wall of the envelope is provided with a cylindrical extension 14 projecting toward the outside and surrounding rod 5. An insulating sleeve 15 of plastic material, in particular polytetrafluoroethylene, is provided to surround the rod 5 inside the extension 14. The inside end of the rod 5 is connected on one side of the screen 13 to the resistor 4 and on the other side of the screen 13 to a capacitor terminal 7, via respective short electrical conductors 16 and 17. Due to the particular configuration of the divider screen 13, and due to the reduced length of the conductors, it is not necessary to use coaxial cables for these electrical connections.

The resistor 4 is selected such that the best response to the input of the amplifier 6 is obtained. The resistance of the resistor 4 is high enough to satisfactorily insulate the generator 2. The resistance is also low enough to permit obtaining a sufficient useful signal at the input of the amplifier 6. This resistance of the resistor 4 is optimally on the order of 1 kiloohm.

The transverse wall 11, opposite that equipped with the rod 5, is penetrated in its central region by a cable 18. This cable has a conductor 19 to supply the circuitry, particularly generator 2, with electrical power. This cable also has a conductor 20 for transmitting the output signal outputted from the detection means 8 to a unit 21. Unit 21 includes an energy source for supplying both the circuitry in the envelope 10 and display means 22 with power. Display means 22 preferably provides a digital readout of the signal level at the output of the detection means 8. The numerical value displayed on the display means comprises the result of the measurement per se.

A means (not shown) is provided to enable applying the probe 5 against the substrate at a constant pressure, with automatic triggering of the measurement once a desired application pressure has been obtained. This means may include a strain gauge placed on the extension 14. This means may also a sliding mount for attaching extension 14 and probe 5 to envelope 10. An elastic means, the compression of which determines the application force desired, would be included between the device and the substrate.

To interface this device with a computer, an oscillator circuit controlled by the amplitude of the signal at the output of the detection means 8 is provided in the envelope 10. The output of this oscillator circuit is connected by a cable to the computer. The period of the signals furnished by the oscillator circuit contains the measurement information transmitted to the computer. The time interval between two leading edges of the signal furnished by the oscillator circuit comprises an image of the voltage of the output of the detection means 8.

The function of the device described above is as follows. Once the device has been actuated, the unit 21 assures the supply of energy to the circuits of the envelope 10. The user then grasps the envelope 10 with one hand and presses the probe 5 against the skin at which the measurement is to be made. The measurement of the water content occurs in a direction substantially orthogonal to the surface of the skin. The user exerts sufficient force on the envelope 10 to obtain the desired pressure of application of the probe 5 to the skin. Reading of the measurement is performed at the display means 22 of the unit 21.

Tests performed with a variable-frequency generator by plunging the sensor probe 5 into a brine has shown that a frequency of 10.7 MHz leads to highly dynamic measurement. This elevated frequency makes it possible to perform a deep measurement of the water content of a substrate.

The physical, metallic separation between the generator 2 and the amplifier 6, on the one hand, and between the generator 2 and the detection means 8 on the other, provides electromagnetic insulation between these components. Accordingly, operation of the amplifier and the detection means is unaffected by radiation from the generator 2.

By adjusting the gain of the generator 2 and amplifier 6, the same response curve can be obtained for different apparatuses. Measurements performed with different apparatuses in brines have made it possible to obtain very close results, with only about 1% deviation. The high input impedance of the amplifier 6 makes it possible to avoid inaccurate measurements due to loading of the generator 2.

The sensor probe 5, which may be a simple rod or stylus, is of reduced bulk and is particularly simple to use. The arrangement of circuitry inside envelope 10, with separation by the screen 13, makes it possible to dispense with a shielded coaxial cable to connect the sensor probe 5 to the generator 2 and to the amplifier 6.

In a variant of the present invention, the power and display devices 21 and 22, respectively, are contained in the measurement head, thereby making the system portable.

What is claimed is:

1. A device for measuring the water content of a substrate, comprising:
    a voltage generator with an output for outputting an alternating voltage signal with a constant frequency and a constant amplitude;
    a conductive probe for making electrical contact with the substrate;
    a resistance means connected between the output of said voltage generator and said probe; and
    an amplitude detector means having an input connected to said probe, the amplitude detector having an output for outputting a signal indicative of the amplitude of an alternating voltage on the probe,
    wherein the voltage generator, the resistance means, and the amplitude detector means are contained in a metallic enclosure with an electromagnetic shield separating the voltage generator from the amplitude detector means.

2. The device of claim 1, wherein said amplitude detector means comprises:
    a voltage amplifier means for amplifying the alternating voltage on said probe; and
    an amplitude detector for receiving the output of the voltage amplifier means and for outputting a signal indicative of the amplitude of said amplified alternating voltage.

3. The device of claim 2, wherein said metallic enclosure is in the form of a cylinder and wherein said electromagnetic shield comprises a metal plate disposed inside said cylinder such that it separates said cylinder into two half-cylinders.

4. The device of claim 3, wherein said probe is located at one end of said cylinder, said resistance means being located on one side of said metal plate and said voltage amplifier means being located on the other side of said metal plate, the resistance means and the voltage amplifier means being located inside the cylinder close to the probe end of the cylinder so that the electrical connections between the resistance means, the voltage amplifier means, and the probe are short.

5. The device of claim 4, further comprising a power supply and display means for powering said voltage generator and said amplitude detector means, and for displaying information indicative of the water content of the substrate based on said signal indicative of the amplitude of the alternating voltage on the probe, wherein the end of said cylinder opposite said probe has an opening through which electrical conductors extend to connect said power supply and display means to circuitry inside said cylinder.

6. The device of claim 5, wherein said information is displayed at least in part in digital form.

7. The device of claim 1, wherein the frequency and the amplitude of the output of the voltage generator remain substantially constant when the probe is connected to substrates with different impedances to ground.

8. The device of claim 1, wherein the resistance of the resistance means is selected so that when said probe is in electrical communication with the substrate said alternating voltage on the probe is of sufficiently high amplitude to be detected, and so that the output of said voltage generator is sufficiently insulated from low impedances to ground caused the substrate's having a low impedance to ground.

9. The device of claim 1, wherein the resistance of the resistance means is on the order of 1 kΩ and the substrate is skin.

10. The device of claim 1, wherein the input of the amplitude detector means has an input impedance on the order of 100 kΩ.

11. The device of claim 1, wherein the frequency output by the voltage generator is greater than 100 kHz.

12. The device of claim 1, wherein the frequency output by the voltage generator is approximately 10.7 MHz and the substrate is skin.

13. The device of claim 1, further comprising a power supply and display means for powering said voltage generator and said amplitude detector means and for displaying information indicative of the water content of the substrate based on said signal indicative of the amplitude of the alternating voltage on the probe.

* * * * *